United States Patent
Chang et al.

(10) Patent No.: US 9,062,009 B2
(45) Date of Patent: Jun. 23, 2015

(54) MACROCYCLIC COMPOUNDS AND METAL COMPLEXES FOR BIOIMAGING AND BIOMEDICAL APPLICATIONS

(71) Applicant: National Yang Ming University, Taipei (TW)

(72) Inventors: Cheng Allen Chang, Taipei (TW); Ren-Shyan Liu, Taipei (TW); Bhalchandra Vishnu Bhagwat, Taipei (TW)

(73) Assignee: National Yang Ming University, Taipei (TW)

( * ) Notice: Subject to any disclaimer, the term of this patent is extended or adjusted under 35 U.S.C. 154(b) by 0 days.

(21) Appl. No.: 13/731,545

(22) Filed: Dec. 31, 2012

(65) Prior Publication Data

US 2014/0187527 A1 Jul. 3, 2014

(51) Int. Cl.
| | |
|---|---|
| *C07D 413/10* | (2006.01) |
| *C07F 5/00* | (2006.01) |
| *A61K 51/04* | (2006.01) |
| *C07D 257/02* | (2006.01) |
| *C07D 273/00* | (2006.01) |
| *C07D 401/14* | (2006.01) |

(52) U.S. Cl.
CPC ............ *C07D 257/02* (2013.01); *C07D 273/00* (2013.01); *C07D 401/14* (2013.01); *A61K 51/0482* (2013.01); *C07F 5/003* (2013.01); *C07D 413/10* (2013.01)

(58) Field of Classification Search
CPC ... C07D 413/10; C07F 5/003; A61K 51/0482
USPC .............. 540/474, 467, 465, 480; 534/10, 16; 514/184
See application file for complete search history.

(56) References Cited

PUBLICATIONS

Rossiter et al. Journal of Inorganic Biochemistry 2009, 103 (1), 64-71.*

* cited by examiner

*Primary Examiner* — Sreeni Padmanabhan
*Assistant Examiner* — Irina Neagu
(74) *Attorney, Agent, or Firm* — Han IP Corporation

(57) ABSTRACT

The present disclosure provides a novel class of macrocyclic compounds and their metal complexes formed with transition metal ion, lanthanide metal ions and other metal ions (e.g., Al, Ga, Y, In, Sn, Tl, Pb and Bi) and their applications in the fields of contrast agents, artificial nucleases, fluorescence probes, nuclear medicines and other biomedical applications in the therapeutics or diagnostics.

11 Claims, 3 Drawing Sheets

MACROCYCLIC COMPOUNDS AND METAL COMPLEXES FOR BIOIMAGING AND BIOMEDICAL APPLICATIONS

TECHNICAL FIELD

The present disclosure relates to macrocyclic compounds and particularly relates to mono- or bi-functional macrocyclic compounds capable of forming metal complex with metal (e.g., transition or lanthanide) ions, processes for their preparation and their use in the fields of contrast agents, artificial nucleases, fluorescence probes, nuclear medicines, and other biomedical applications in the therapeutics or diagnostics.

BACKGROUND

Applications of macrocyclic metal complexes are numerous. In the field of artificial metallonucleases, it's a challenge to cleave DNA or RNA at specific site for further development in genetic engineering. To achieve this goal, it is very important to understand interactions of metal complexes with large structured RNA or DNA molecule, which are dependent on the selective binding of metal complexes to specific RNA or DNA sites and subsequent hydrolysis reactions. In this regards, the macrocyclic ligands and their substituents play a key role in providing specific binding with nucleic acids (DNA or RNA molecules) and hydrolysis reactions (Bridger, G. J. et. al, *J. Med. Chem.* 1999, 42, 3971-81; New, K. et al., *J. Am. Chem. Soc.* 2008, 130, 14861-71; Rossiter, C. S. et al., *J. Inorg Biochem* 2009, 103, 64-71; Chang C. A. et al., *Inorg. Chem.* 2005, 44, 6646-54). Macrocyclic ligands also play an important role in the field of nuclear medicine by forming stable metal complexes with various radionuclei (WO2011031073). Tetraaza complexes formed between linear or macrocyclic amines and radioactive rhodium-105 have been used in diagnostics and therapeutics (Bounsall, E. J. et al., *Canadian J. of chemistry* 1970, 48, 1481; U.S. Pat. No. 5,489,425). A cobalt complex, [Co(III)(cyclen)Cl$_2$]Cl, has been found to be selectively cytotoxic to human leukemia cells (He, Z. et al., *J. Pharmacology* 2010, 637, 11-15). In medical diagnostics, macrocyclic ligand-metal complexes have been widely used as contrast agents (WO2011031073; U.S. Pat. No. 5,482,699; U.S. Patent Application Publication 2011/0177002). For example, a $^{64}$Cu-tetraaza complex has been used for imaging tumor U87MG, and tetraaza-$^{99m}$Tc complexes have been used in diagnostics (Cai, W. et al., *Eur. J. Nucl. Med. Mol. Imaging.* 2007, 34, 850-858; Troutner, D. E. et al., *J Nucl Med* 1980, 21, 443-448). Furthermore, many gadolinium complexes have been commercialized with trade names, Magnevist, MultiHance, Omniscan, OptiMARK, ProHance, and Dotarem, as magnetic resonance imaging (MRI) contrast agents for diagnostics in daily practice (Caravan, P. et al., *Chem. Rev.* 1999, 99, 2293-2352; Kumar. K. et al., *Inorg. Chem.* 1993, 32, 4193-4199). Among these, ProHance and Dotarem are tetraaza-based (e.g. DO3A and DOTA) macrocyclic ligands. In the case of prodrug-procontrast, macrocyclic ligand-metal complexes can deliver prodrugs into the targeted cancer cells, thus reducing the toxic dose of active drugs. Simultaneously, they also act as contrast agents allowing the measurement of drug activity in the body. The efficiency of the whole process is dependent on the metal complexes and ultimately on the ligands employed (Frullano, L. et al., *Inorg. Chem.* 2006, 45, 8489-8491).

Accurate diagnosis needs effective imaging outcome, which is dependent on the characteristics of contrast agents and ultimately is dependent on the characteristics of ligands. Therefore, there remains a need in developing novel ligands for better imaging in MRI studies to avoid confusing situations in identification, investigation and effective treatment of diseases. In artificial metallonuclease or fluorescence probe areas, it is also essential to develop novel ligands to effectively cleave nucleic acid at a desirable site or to function as efficient fluorescence probes.

SUMMARY

In one aspect, macrocyclic compounds are provided. The compounds of the present disclosure have the following formula (I):

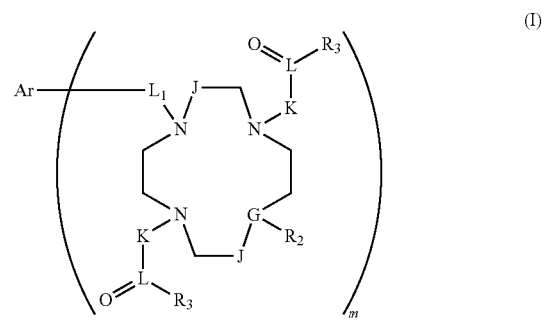

(I)

or an enantiomer, a tautomer, a pharmaceutically acceptable salt, or a prodrug thereof;

wherein:

Ar is an aryl or a heterocyclic ring optionally substituted with —R$_1$;

G is N, O, or S;

J is —CH$_2$—, or —CH$_2$CH$_2$—;

L$_1$ is —CH$_2$—, or —CH$_2$CH$_2$—;

K is H, —CH$_2$—, or —CH$_2$CH$_2$—;

L is —C—, —S(O)—, or —P(OH)—, when K is not H;

each R$_1$ is independently —(CH$_2$)$_n$OR$_4$, —(CH$_2$)$_n$SR$_4$, —(CH$_2$)$_n$N(R$_4$)R$_5$, —(CH$_2$)$_n$NHN(R$_4$)R$_5$, —(CH$_2$)$_n$C(O)OR$_4$, —(CH$_2$)$_n$-alkyl, —(CH$_2$)$_n$-aryl, —(CH$_2$)$_n$-alkenyl, —(CH$_2$)$_n$-alkynyl, —(CH$_2$)$_n$—N$_3$, —(CH$_2$)$_n$—C(O)N(R$_4$)R$_5$, —(CH$_2$)$_n$—S(O)$_2$N(R$_4$)R$_5$, or —(CH$_2$)$_n$—P(O)(OR$_4$)$_2$;

each R$_2$ is absent when G is O or S, or is independently H, optionally substituted alkyl, optionally substituted cycloalkyl, or —CH$_2$R$_7$;

each R$_3$ is independently —OH, or —NHR$_6$;

each R$_4$ and R$_5$ are same or different and independently H, alkyl, or aryl;

each R$_6$ is independently H, optionally substituted alkyl, optionally substituted alkenyl, optionally substituted alkynyl, optionally substituted aryl, or optionally substituted heterocyclic;

each R$_7$ is independently cycloalkyl, aryl, or heterocyclic;

m is 2, 3, or 4; and each n is 0, 1, 2, or 3, and with the proviso that if m is 2, Ar is phenyl, K is H, and R$_2$ is H or absent, then G is not N or O.

In one embodiment, the compound of formula (I) may be a compound of formula (II):

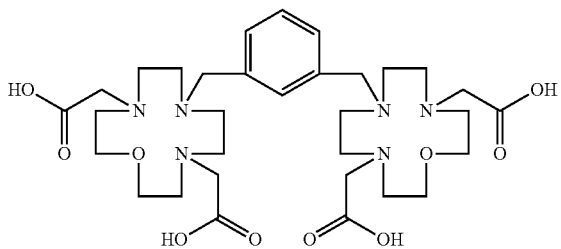

(II)

In one embodiment, the compound of formula (I) may be a compound of formula (III):

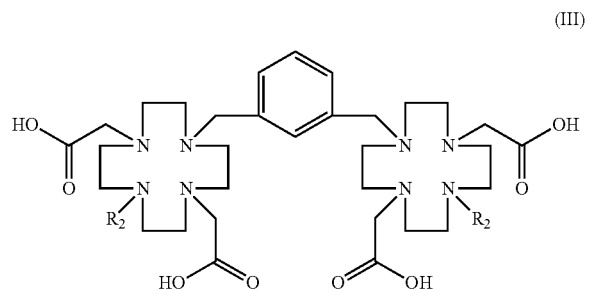

(III)

wherein $R_2$ is methyl, p-methoxybenzyl, or 6-methyl-pyridien-2-carboxylic acid.

In some embodiments, the compound of formula (I) may further comprise at least one group of formula (IV):

(IV)

that bounds the compound of formula (I) to a biomolecule.

wherein: W is —O—, —S—, —CH$_2$—, —SO—, SO$_2$—, —CO—, —NHNH—, —CONH—, —NHCO—, —NH-CONH—, —CONHCO—, —NHCONHO—, —COO—, —COCH$_2$—, —CH$_2$CO—, —NHO—, —ONH—, —CH=CH—, —CH$_2$NH—, —NHCH$_2$—, —NH—, —NR$_8$, —NH(C=NH)NH—, —CH=N—, —CH=N—O—, —N=CH—, —SO$_2$NH—, —NHSO$_2$—, —NH—CS—, —NHCSNH—, —NH(C=NH)NH—O—, —OCO—, —S—S—, —N=N—, alkynyl, methylene carbamate, methylene thiocarbamate, methylene isourea, methylene isothiourea, methylene guanidine, —C=C(R$_8$)—COOR$_8$, —C=C(R$_8$)—COR$_8$, —C=NH—, —C=NOH, —C=NR$_8$, —C=NOR$_8$, allyl-OCOR$_8$, allyl ester, phenylene, alkylene, ethynydiyl, ethylenediyl, a polymerizable group, a boron, a silicon, phosphorous, selenium, haloacetamido, isothiocyanate, maleimido, dichlorotriazinylamino, dichlorotriazinyl, thioester, pyridyldithio, aminooxy, amino, hydrazide, carboxylic acid, or acid halide;

$R_8$ is alkyl, cycloalkyl, or aryl;

X and Y are same or different and independently alkyl, cycloalkyl, aryl, or heterocylic, wherein any two carbon atoms are optionally interrupted with one or more N, O, S, Si, P, Se or B; and s, t, and p are an integer from 0 to 100.

In some embodiments, the X and Y may further comprise positively charged carboxylate or negatively charged ammonium moieties.

In some embodiments, the biomolecule may be proteins, protein-proteins, oligopeptides, oligonucleotides, DNA, RNA, haptens, antibodies, bleomycins, modified oligopeptides or oligonucleotides, sugar- or base-modified protein, oligonucleotide or polynucleotide, oligo-saccharide, polysaccharide, PNA, LNA, drug, phosphoslipide, lectine, receptor binding ligand, polymers, proteoglycans, liposomes, aerogels, steroids, microorganisms, hormones dendrimers, nanoparticles, microparticles, or amyloid binding moieties.

In some embodiments, the modified oligopeptides or oligonucleotides may be phosphoroamidate, phosphoromonothioate, or a phosphorodithioate, and the polymers may be polyethyleneglycol or polylysine.

In another aspect, metal complexes of compounds of formula (I) are provided. The metal complexes may comprise metal ions and a compound of formula (I) as set forth above.

In some embodiments, the metal ions may comprise transition metal ions, lanthanide metal ions, Al, Ga, Y, In, Sn, Tl, Pb, or Bi ions.

In some embodiments, the metal ions may be radioactive isotopes comprising Cr-51, Ga-66, Ga-67, Ga-68, Y-90, In-111, Ce-134, Nd-140, Eu-157, Sm-153, Tb-161, Dy-165, Ho-166, Ho-166, Er-169, Lu-177, Er-165, or Ho-161.

In another aspect, pharmaceutical compositions comprising pharmaceutically acceptable carriers and compounds of formula (I) or metal complexes that comprise metal ions and compounds of formula (I) are provided.

In another aspect, a method of making compound of formula (I) is provided. The method may comprise: reacting a compound of formula (V):

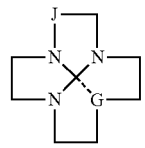

wherein J is —CH$_2$—, or —CH$_2$CH$_2$—; G is N, O or S;

or a compound of formula (VI):

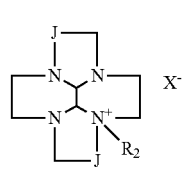

(VI)

wherein $R_2$ is independently H, optionally substituted alkyl, optionally substituted cycloalkyl, or —CH$_2$R$_7$; $R_7$ is independently cycloalkyl, aryl, or heterocyclic; and X is fluoro, chloro, or bromo;

with Ar dibromide, wherein Ar is an aryl or a heterocyclic ring optionally substituted with —R$_1$; R$_1$ is independently —(CH$_2$)$_n$OR$_4$, —(CH$_2$)$_n$SR$_4$, —(CH$_2$)$_n$N(R$_4$)R$_5$, —(CH$_2$)$_n$NHN(R$_4$)R$_5$, —(CH$_2$)$_n$C(O)OR$_4$, —(CH$_2$)$_n$-alkyl, —(CH$_2$)$_n$-aryl, —(CH$_2$)$_n$-alkenyl, —(CH$_2$)$_n$-alkynyl, —(CH$_2$)$_n$—N$_3$, —(CH$_2$)$_n$—C(O)N(R$_4$)R$_5$, —(CH$_2$)$_n$—S(O)$_2$N(R$_4$)R$_5$, or —(CH$_2$)$_n$—P(O)(OR$_4$)$_2$; R$_4$ and R$_5$ are same or different and independently H, alkyl, or aryl; and each n is 0, 1, 2, or 3; and reducing the resulting salt under suitable conditions to form a compound of formula (VII):

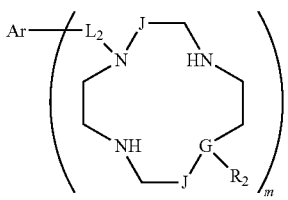

(VII)

wherein:

Ar is an aryl or a heterocyclic ring optionally substituted with —$R_1$;

G is N, O, or S;

J is —$CH_2$—, or —$CH_2CH_2$—;

$L_1$ is —$CH_2$—, or —$CH_2CH_2$—;

each $R_1$ is independently —$(CH_2)_nOR_4$, —$(CH_2)_nSR_4$, —$(CH_2)_nN(R_4)R_5$, —$(CH_2)_nNHN(R_4)R_5$, —$(CH_2)_nC(O)OR_4$, —$(CH_2)_n$-alkyl, —$(CH_2)_n$-aryl, —$(CH_2)_n$-alkenyl, —$(CH_2)_n$-alkynyl, —$(CH_2)_n$—$N_3$, —$(CH_2)_n$—$C(O)N(R_4)R_5$, —$(CH_2)_n$—$S(O)_2N(R_4)R_5$, or —$(CH_2)_n$—$P(O)(OR_4)_2$;

each $R_2$ is absent when G is O or S, or is independently H, optionally substituted alkyl, optionally substituted cycloalkyl, or —$CH_2R_7$;

each $R_4$ and $R_5$ are same or different and independently H, alkyl, or aryl;

each $R_7$ is independently cycloalkyl, aryl, or heterocyclic;

m is 2, 3, or 4; and each n is 0, 1, 2, or 3.

In another aspect, a method of acquiring an image is provided. The method may comprises: administrating to an issue, cell, or mammal an effective amount of a metal complex comprising metal ions and a compound of formula (I); and acquiring a magnetic image of the cell, tissue or mammal.

In yet another aspect, a method of cleaving a nucleic acid is provided. The method may comprise using a metal complex of comprising metal ions and a compound of formula (I).

BRIEF DESCRIPTION OF DRAWINGS

The foregoing aspects and many of the attendant advantages of the embodiments of present disclosure will become more readily appreciated as the same become better understood by reference to the following detailed description, when taken in conjunction with the accompanying drawings, wherein.

DETAILED DESCRIPTION OF VARIOUS EMBODIMENTS

Figure 1:
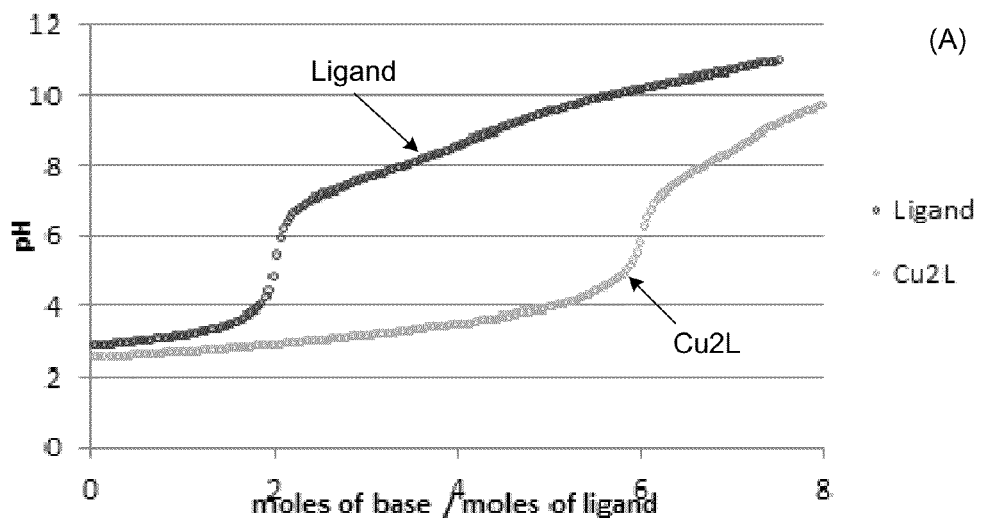
FIG. 1A is a graph showing the titration curve of Dimer-$12N_3O$ with $Cu^{2+}$ ion by standard base.
FIG. 1B is a graph showing titration curves of Dimer-$12N_3O$ with $Cu^{2+}$ and $Zn^{2+}$ ions.
Figure 1:
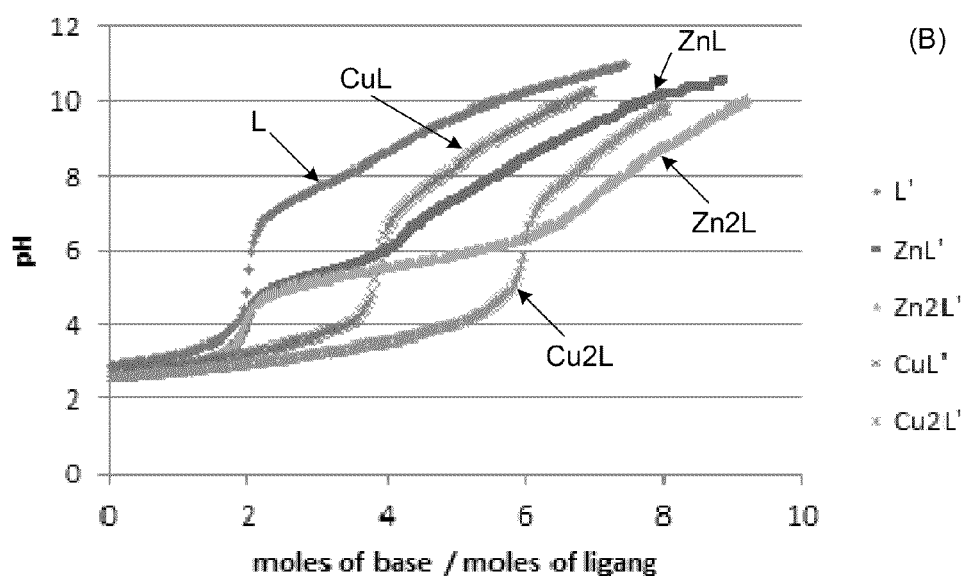

The present disclosure provides mono- or bi-functional macrocyclic compounds and their metal complexes that are useful in various biomedical fields, including contrast agents in MRI studies, artificial nuclease to cleave phosphodiester bond of DNA and RNA molecules, fluorescence probes, and nuclear medicines.

As used herein, "R" refers to a substituent on an atom. Unless otherwise specifically assigned, R represents any single atom or any one of the substituent groups defined below. When there is more than one R in a molecule, the "R" may independently at each occurrence refer to a single atom or any one of the substituent groups defined below.

"Alkyl" refers to C1-C20 straight chain and branched alkyl groups. Representative straight chain alkyl groups include methyl, ethyl, n-propyl, n-butyl, n-pentyl, and n-hexyl groups. Unless stated otherwise in the specification, an alkyl group may be optionally substituted by one of the following groups: —$(CH_2)_nOR_5$, —$(CH_2)_nSR_5$, —$(CH_2)_nN(R_5)R_6$, —$(CH_2)_nNHN(R_5)R_6$, —$(CH_2)_nC(O)OR_5$, —$(CH_2)_n$-alkyl, —$(CH_2)_n$-aryl, —$(CH_2)_n$-alkenyl, —$(CH_2)_n$-alkynyl, —$(CH_2)_n$—$N_3$, —$(CH_2)_n$—$C(O)N(R_5)R_6$, —$(CH_2)_n$—$S(O)_2N(R_5)R_6$, or —$(CH_2)_n$—$P(O)(OR_5)_2$, where n is 0, 1, 2, or 3 and $R_5$ and $R_6$ are same or different and independently alkyl, or aryl.

"Alkenyl" refers to a straight or branched hydrocarbon chain containing at least one double bond and having 2 to 10 carbon atoms. Representative alkenyl groups include ethenyl, propylenyl, 1-butenyl, 2-butenyl, isobutylenyl, and 2,3-dimethyl-2-butenyl groups. The alkenyl group may be optionally substituted as defined above for the alkyl group.

"Alkynyl" refers to a straight or branched hydrocarbon chain containing at least one triple bond and having 2 to 10 carbon atoms. Representative alkynyl groups include ethynyl, propynyl, and 1-butynyl groups. The alkynyl group may be optionally substituted as defined above for the alkyl group.

"Aryl" refers to aromatic monocyclic or multicyclic hydrocarbon ring system consisting only of hydrogen and carbon and containing from 6 to 19 carbon atoms in the ring portion. Representative aryl groups include phenyl, biphenyl, naphthyl, and anthracenyl groups. The aryl group may be optionally substituted as defined above for the alkyl group.

"Cycloalkyl" refers to a non-aromatic, monocyclic or polycyclic ring comprising carbon and hydrogen atoms. Representative cycloarkyl groups include cyclopropyl, cyclopentyl groups. The cycloalkyl group may be optionally substituted as defined above for the alkyl group.

"Complex" and "metal complex" refer to a compound of the present disclosure, e.g. Formula (I), complexed or coordinated with a metal.

"Enantiomers" refer to two stereoisomers whose molecules are nonsuperimposable mirror images of one another. A "stereoisomer" refers to a compound made up of the same atoms bonded by the same bonds but having different three-dimensional structures, which are not interchangeable.

"Heterocyclic" means aromatic groups that include one or more heteroatoms (e.g., oxygen, nitrogen, sulfur, or phosphorus) in the aromatic ring. Representative heteroaromatic groups that include a single heteroatom in the aromatic ring include furanyl, pyridinyl, pyrrolyl, and thiophenyl groups. Representative heteroaromatic groups that include more than one heteroatom in the aromatic ring include $C_4N_2$, $C_3N_3$, $C_3N_2$, $C_3NO$, $C_3NS$, and $C_2N_3$ groups. The heterocyclic group may be optionally substituted as defined above for the alkyl group.

"Halogen" or "halo" refers to bromo, chloro, fluoro, or iodo.

"Mammal" includes humans and domestic animals, such as cats, dogs, cattle, rabbits, mice, rats, and the like.

"Optional" or "optionally" means that the subsequently described event of circumstances may or may not occur, and that the description includes instances where the event of circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts.

A "pharmaceutical composition" refers to a formulation of a compound of the disclosure and a medium generally accepted in the art for the delivery of the biologically active compound to mammals, e.g., humans. Such a medium includes all pharmaceutically acceptable carriers, diluents or excipients therefor.

"Prodrug" is meant to indicate a compound that may be converted under physiological conditions or by solvolysis to a biologically active compound of the invention. Thus, the term "prodrug" refers to a metabolic precursor of a compound that is pharmaceutically acceptable. A prodrug may be inactive when administered to a subject in need thereof, but is converted in vivo to an active compound. Prodrug is typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam).

A "tautomer" refers to a proton shift from one atom of a molecule to another atom of the same molecule. The present disclosure includes tautomers of any said compound.

In one aspect, macrocyclic compounds are provided. The compounds of the present disclosure have the following formula (I):

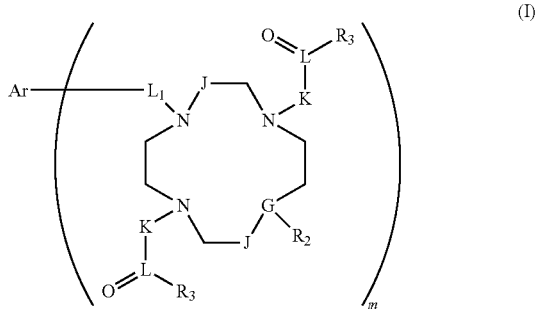

(I)

or an enantiomer, a tautomer, a pharmaceutically acceptable salt, or a prodrug thereof.

In formula (I), Ar is an aryl or a heterocyclic ring optionally substituted with —$R_1$; G is N, O, or S; J is —$CH_2$—, or —$CH_2CH_2$—; $L_1$ is —$CH_2$—, or —$CH_2CH_2$—; K is H, —$CH_2$—, or —$CH_2CH_2$—; L is —C—, —S(O)—, or —P(OH)—, when K is not H; each $R_1$ is independently —$(CH_2)_nOR_4$, —$(CH_2)_nSR_4$, —$(CH_2)_nN(R_4)R_5$, —$(CH_2)_nNHN(R_4)R_6$, —$(CH_2)_nC(O)OR_4$, —$(CH_2)_n$-alkyl, —$(CH_2)_n$-aryl, —$(CH_2)_n$-alkenyl, —$(CH_2)_n$-alkynyl, —$(CH_2)_n$—$N_3$, —$(CH_2)_n$—C(O)N($R_4$)$R_6$, —$(CH_2)_n$—S(O)$_2$N($R_4$)$R_6$, or —$(CH_2)_n$—P(O)(O$R_4$)$_2$; each $R_2$ is absent when G is O or S, or is independently H, optionally substituted alkyl, optionally substituted cycloalkyl, or —$CH_2R_7$; each $R_3$ is independently —OH, or —NH$R_6$, each $R_4$ and $R_5$ are same or different and independently H, alkyl, or aryl; each $R_6$ is independently H, optionally substituted alkyl, optionally substituted alkenyl, optionally substituted alkynyl, optionally substituted aryl, or optionally substituted heterocyclic; each $R_7$ is independently cycloalkyl, aryl, or heterocyclic; m is 2, 3, or 4; and each n is 0, 1, 2, or 3; with the proviso that if m is 2, Ar is phenyl, K is H, and $R_2$ is H or absent, then G is not N or O.

In one embodiment, the compound of formula (I) is a compound of formula (II)

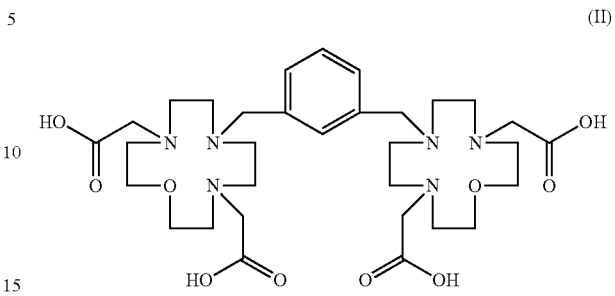

(II)

In one embodiment, the compound of formula (I) is a compound of formula (III)

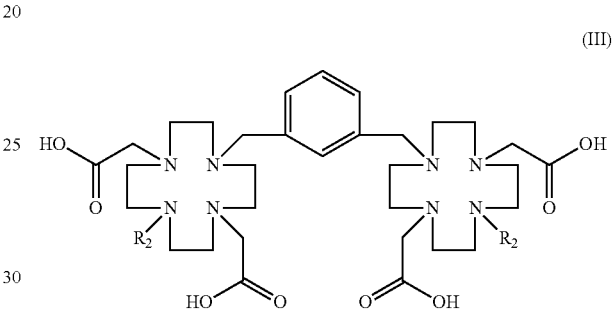

(III)

Preferably, $R_2$ is methyl, p-methoxybenzyl, or 6-methyl-pyridien-2-carboxylic acid.

In some embodiments, the compound of formula (I) may comprise at least one group of formula (IV):

—W—(X$_s$—Y$_t$)$_p$—  (IV)

that bounds the compound of formula (I) to a biomolecule.

In formula (IV), W is —O—, —S—, —CH$_2$—, —SO—, SO$_2$—, —CO—, —NHNH—, —CONH—, —NHCO—, —NHCONH—, —CONHCO—, —NHCONHO—, —COO—, —COCH$_2$—, —CH$_2$CO—, —NHO—, —ONH—, —CH═CH—, —CH$_2$NH—, —NHCH$_2$—, —NH—, —NR$_8$, —NH(C═NH)NH—, —CH═N—, —CH═N—O—, —N═CH—, —SO$_2$NH—, —NHSO$_2$—, —NH—CS—, —NHCSNH—, —NH(C═NH)NH—O—, —OCO—, —S—S—, —N═N—, alkynyl, methylene carbamate, methylene thiocarbamate, methylene isourea, methylene isothiourea, methylene guanidine, —C═C(R$_8$)—COOR$_8$, —C═C(R$_8$)—COR$_8$, —C═NH—, —C═NOH, —C═NR$_8$, —C═NOR$_8$, allyl-OCOR$_8$, allyl ester, phenylene, alkylene, ethynydiyl, ethylenediyl, a polymerizable group, a boron, a silicon, phosphorous, selenium, haloacetamido, isothiocyanate, maleimido, dichlorotriazinylamino, dichlorotriazinyl, thioester, pyridyldithio, aminooxy, amino, hydrazide, carboxylic acid, or acid halide; R$_8$ is alkyl, cycloalkyl, or aryl; X and Y are same or different and independently alkyl, cycloalkyl, aryl, or heterocyclic, wherein any two carbon atoms are optionally interrupted with one or more N, O, S, Si, P, Se or B; and s, p, and t are an integer from 0 to 100.

In some embodiment, the biomolecule may comprise proteins, protein-proteins, oligopeptides, oligonucleotides, DNA, RNA, haptens, antibodies, bleomycins, modified oligopeptides or oligonucleotides, sugar- or base-modified protein, oligonucleotide or polynucleotide, oligo-saccharide, polysaccharide, PNA, LNA, drug, phospholipide, lectine, receptor binding ligand, polymers, proteoglycans, liposomes, aerogels, steroids, microorganisms, hormones dendrimers, nanoparticles, microparticles, or amyloid binding moieties.

Preferably, the modified oligopeptides or oligonucleotides are phosphoroamidate, phosphoromonothioate, or phosphorodithioate. Preferably, the polymers are polyethyleneglycol or polylysine.

In another aspect, metal complexes are provides. The metal complexes of the present disclosure may comprise metal ions and compounds of formula (I) as set forth above.

Preferably, the metal ions are transition metal ions, lanthanide metal ions, Al, Ga, Y, In, Sn, Tl, Pb, or Bi ions.

The metal complexes of compounds of formula (I) with various radioactive isotopes are useful in positron emission tomography (PET) to diagnose disease. Preferably, the radioactive isotopes comprising Cr-51, Ga-66, Ga-67, Ga-68, Y-90, In-111, Ce-134, Nd-140, Eu-157, Sm-153, Tb-161, Dy-165, Ho-166, Ho-166, Er-169, Lu-177, Er-165, or Ho-161.

Compounds of formula (I) and their metal complexes as set forth above can be applied in the various fields such as, as a contrast agent or molecular probe in imaging studies (MRI, optical, etc.), as artificial nuclease/hydrolase/peptidase to cleave phosphodiester bond of DNA and RNA molecules or peptide bond, as a nuclear medicine, or applied in other biomedical applications (therapeutics and diagnosis).

In another aspect, the present disclosure provides pharmaceutical compositions comprising pharmaceutically acceptable carriers and compounds of formula (I) or metal complexes of compounds of formula (I) as set forth above.

The pharmaceutically acceptable carrier, also known in the art as an excipient, vehicle, auxiliary, adjuvant, or diluent, is typically a substance which is pharmaceutically inert, confers a suitable consistency or form to the composition, and does not diminish the therapeutic or diagnostic efficacy of the conjugate. The carrier is generally considered to be "pharmaceutically acceptable" if it does not produce an unacceptably adverse, allergic or other untoward reaction when administered to a mammal, especially a human.

The selection of a pharmaceutically acceptable carrier will also, in part, be a function of the route of administration. In general, the metal complexes of the present disclosure can be formulated with conventional pharmaceutically acceptable carriers for any route of administration so long as the target tissue is available via that route. For example, suitable routes of administration include, but are not limited to, oral, parenteral (e.g., intravenous, intraarterial, subcutaneous, subcutaneous, intramuscular, intracapsular, intraspinal, or intraperitoneal), intravesical, intrathecal, enteral, pulmonary, intralymphatic, intracavital, transurethral, intradermal, intramammary, buccal, orthotopic, intralesional, percutaneous, endoscopical, transmucosal, and intestinal administration.

Pharmaceutically acceptable carriers for use in the compositions of the present disclosure are well known to those of ordinary skill in the art and are selected based upon a number of factors: the particular complex used, and its concentration, stability and intended bioavailability; the disease, disorder or condition being diagnosed with the composition; the subject, its age, size and general condition; and the route of administration. Suitable pharmaceutically acceptable carriers include those that are suitable for injection such as aqueous buffer solutions; e.g., tris(hydroxymethyl)amino methane (and its salts), phosphate, citrate, bicarbonate, etc., sterile water for injection, physiological saline, and balanced ionic solutions containing chloride and/or bicarbonate salts of normal blood plasma cations such as Ca, Na, K and Mg, and other halides, carbonates, sulphates, phosphates of Na, K, Mg, Ca. The vehicles may advantageously contain a small amount (e.g., from about 0.01 to about 15.0 mole %) of a chelating agent such as ethylenediamine tetraacetic acid (EDTA), calcium disodium EDTA, or other pharmaceutically acceptable chelating agents such as calcium monosodium DTPA-BMEA (Versetamide; Mallinckrodt Inc.). The composition may further comprise non-radiographic additives selected from the group consisting of excipients, such as, for example, glycerol, polyethylene glycol or dextran, and anticlotting agents, such as, for example, heparin or hirudin. A thorough discussion of pharmaceutically acceptable carriers, diluents, and other excipients is presented in REMINGTON'S PHAEPHACEUTICAL SCIENCES (Mack Pub. Co., N.J. current edition).

In another aspect, the present disclose provides a method of acquiring an image that may comprises administrating to a tissue, cell, or mammal an effective amount of a compound of formula (I) or a metal complex of compound of formula (I) as set forth above and acquiring a magnetic image of the cell, tissue or patient.

In another aspect, the present disclose provide a method of cleaving a nucleic acid using a compound of formula (I) or a metal complex of compound of formula (I) as set forth above.

In particular, compounds of formula (I) of the present disclosure may be prepared by the following Schemes. It is understood that other compounds of the present disclosure may be prepared in a similar manner as described below or by methods known to one of ordinary skill in the art.

Compound 9 (12N₃O) and Compound 10 (Cyclen) are intermediates in the preparation of compounds of formula (I). They are prepared as described blew in Scheme 1. First, Compounds diethyleneglycol (1), diethylenetriamine (2), and bis-(2-Hydroxy-ethyl)-amine (3) are protected and converted into their corresponding tosylated derivatives, Compound 4 (1,5-ditosyloxy-3-oxapentane), Compound 5 (N,N',N"-tritosyldiethylenetriamine), and Compound 6 (bis-(2-Tosyloxy-ethyl)-methylamine)), respectively, using tosyl chloride. Compound 5 is then reacted with sodium hydride to obtain corresponding salt. Reacting the resulting salt of Compound 5 with Compound 4 or Compound 6 affords cyclized Compound 7 (12N3Ts3O) or Compound 8 (12N4Ts4), respectively. Compound 7 and Compound 8 are deprotected using concentrated sulphuric acid to get corresponding Compound 9 (12N₃O) and Compound 10 (cyclen).

SCHEME 1

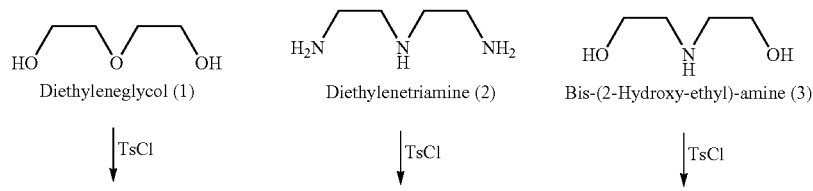

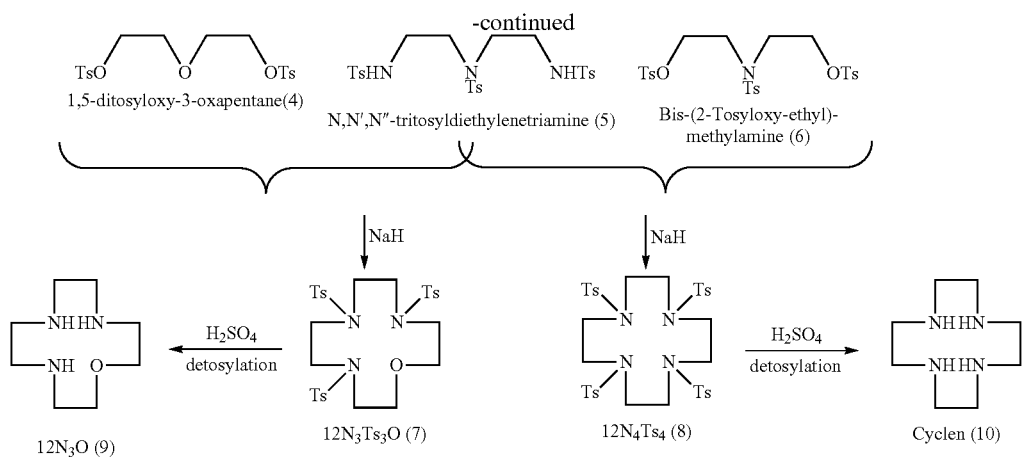

Referring to the following Scheme 2, further protection of Compound 9 with dimethyl acetal yields Compound 11 (12N$_3$O-tricyclic form), which is then reacted with m-xylene dibromide to afford Compound 12 (Dimer-12N$_3$O-tricyclic form). Followed by deprotection, Compound 13 (Dimer-12N$_3$O) is alkylated to give Compound 14 (dimer-ODO2A 14).

SCHEME 2

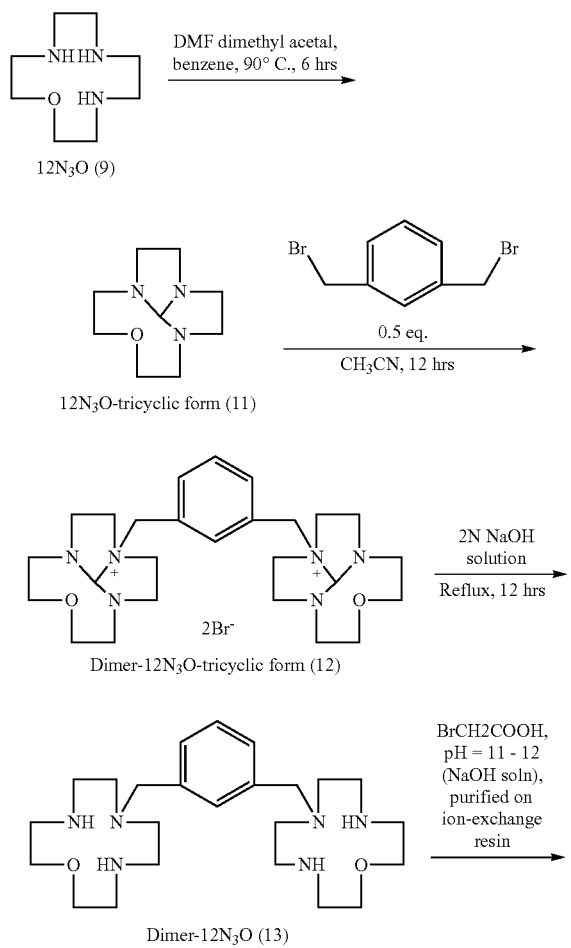

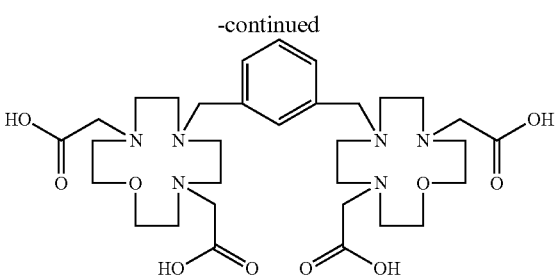

General procedures A and B are employed to synthesize cyclen-containing compounds of formula (I). Referring to the following Scheme 3, Compounds 19 and 24 are prepared according to the general procedure A. Initially, Compound 10 (cyclen) is protected with glyoxal to give Compound 15. Compound 15 is then reacted with alkyaryl or alkyl halide (RX) to yield Compound 16 and Compound 21, respectively. Compound 16 or Compound 21 is reacted with m-xylene dibromide to obtain Compound 17 or Compound 22, respectively. Compound 17 or Compound 22 is then deprotected with hydrazine to yield Compound 18 or Compound 23, respectively. Finally, Compound 18 or Compound 23 is alkylated to yield Compound 19 or Compound 24, respectively. R may be methyl or p-methoxy benzyl substituent.

SCHEME 3

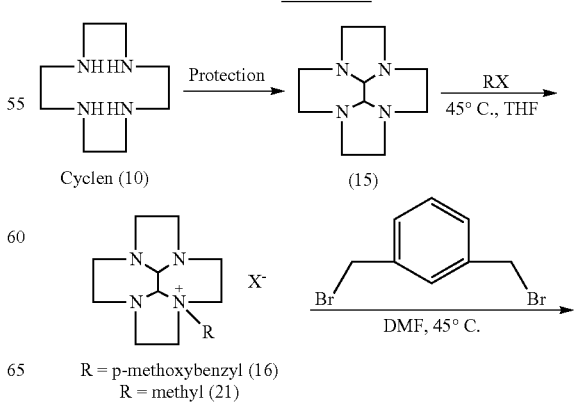

SCHEME 4
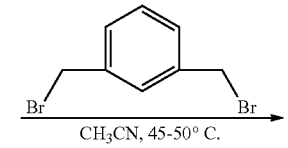
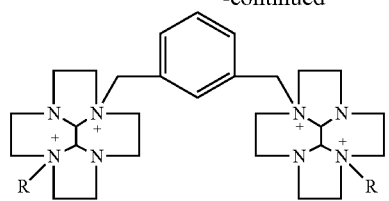
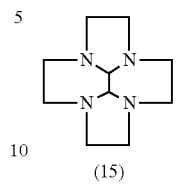
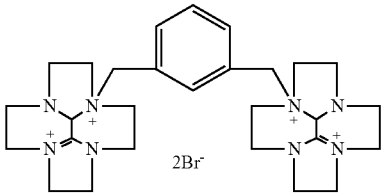
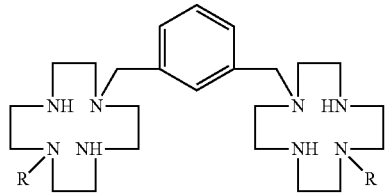
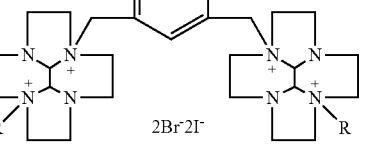
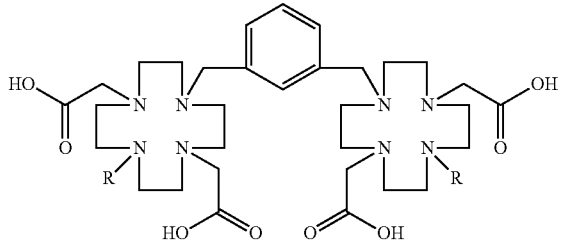
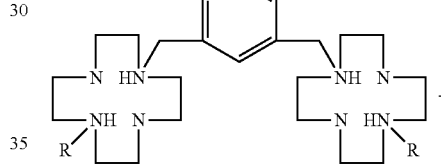
Another approach to synthesize Compound 24 by procedure B is illustrated in the following Scheme 4. First, m-xylene dibromide is reacted with protected Compound 15 to obtain Compound 20. Reacting Compound 20 with methyl iodide affords Compound 22. After deprotection and alkylation, Compound 24 is obtained through Compound 23.
R = CH₃
SCHEME 5
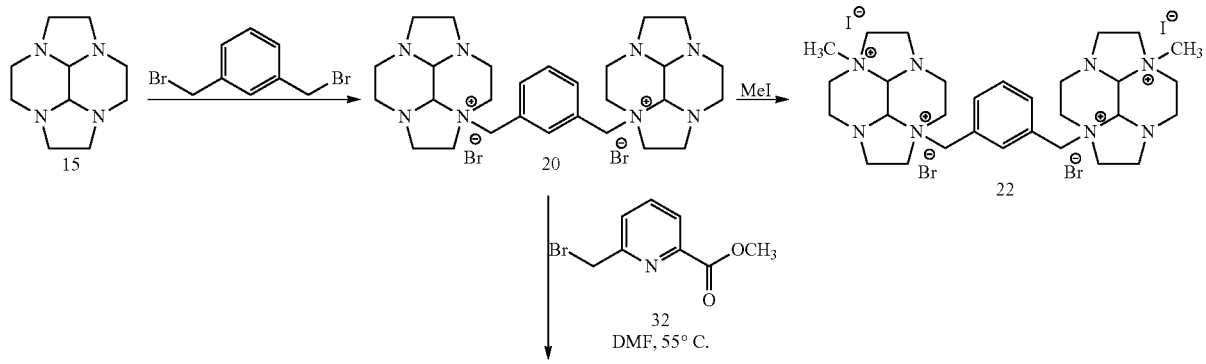
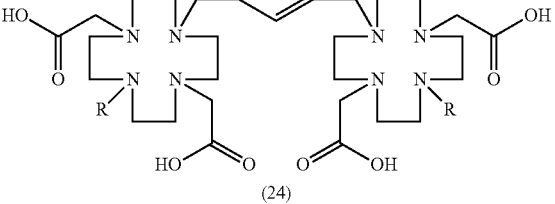

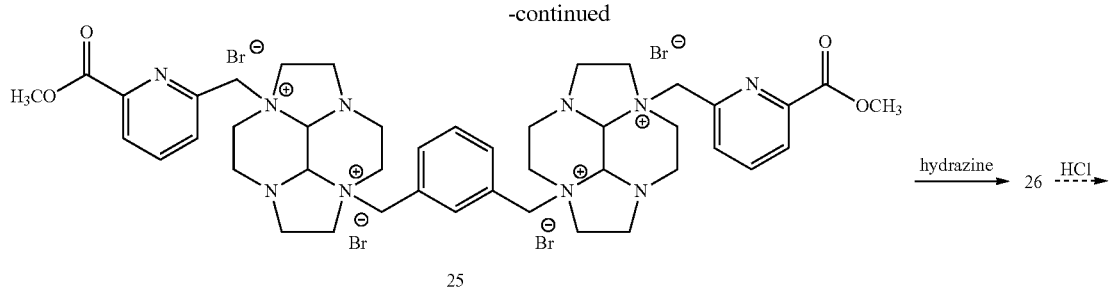

25

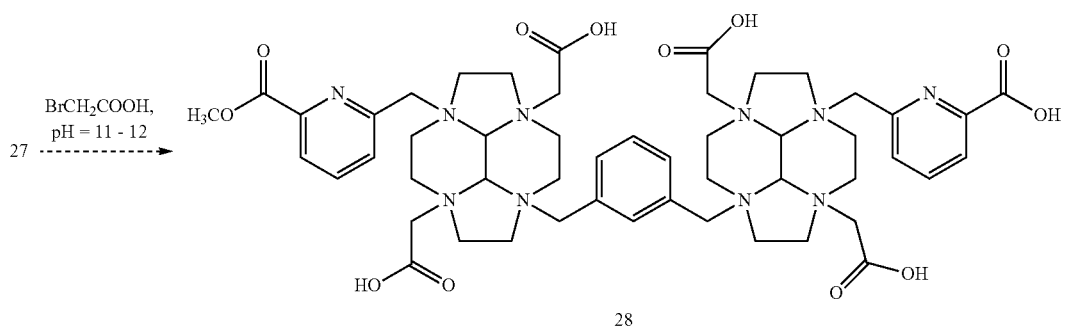

28

Using general procedure B, Compound 28 of formula (I) is prepared as described in Scheme 5. Compound 22 is reacted with Compound 32 first to obtain Compound 25. After deprotection and hydrolysis, Compound 28 is obtained by alkylation of Compound 27 using bromoacetic acid under basic condition.

The synthesis of intermediate Compound 32 is shown in the following Scheme 6. Pyridine-2,6-dicarboxylic acid is treated with thionyl chloride in methanol to obtain its diester compound 30, which is partially reduced with sodium borohydride to get Compound 31. Compound 31 is then reacted with phosphorous tribromide to yield compound 32.

SCHEME 6

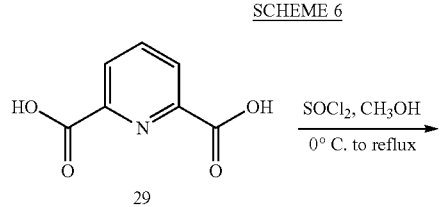

29

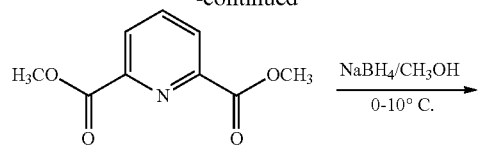

Compound 37 of formula (I) is prepared according to a general procedure C as described below in Scheme 7. First, Compound 20 is converted to Compound 35 via the protection-deprotection transformations through compound 33 and 34, then it is alkylated to obtain compound 36 and finally formyl protection is removed to obtain Compound 37.

SCHEME 7

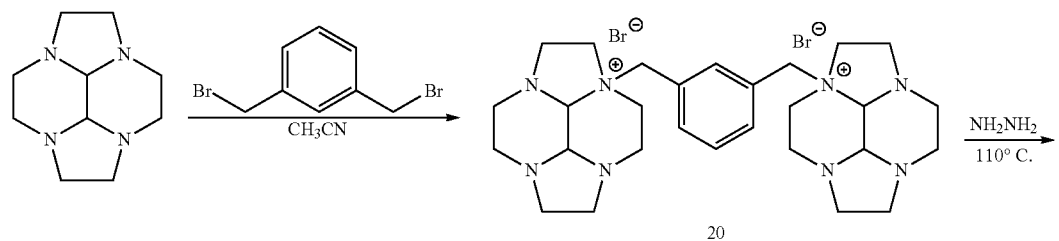

20

17
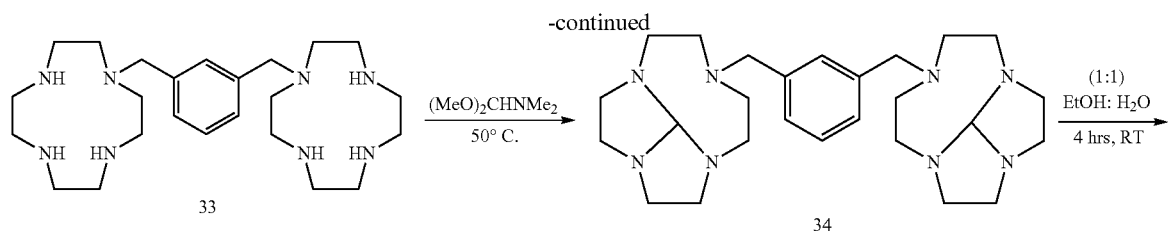
18
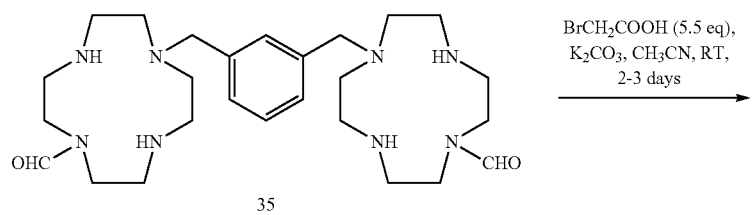
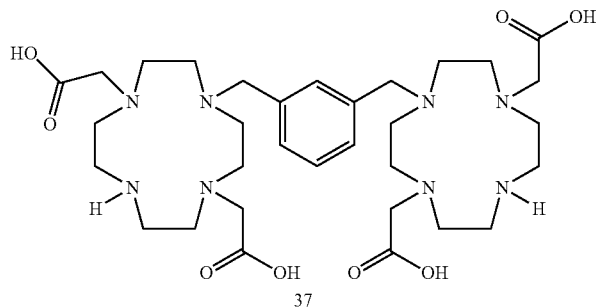
An example of preparing a bioconjugate of a compound of formula (I) is described below in Scheme 8.
SCHEME 8
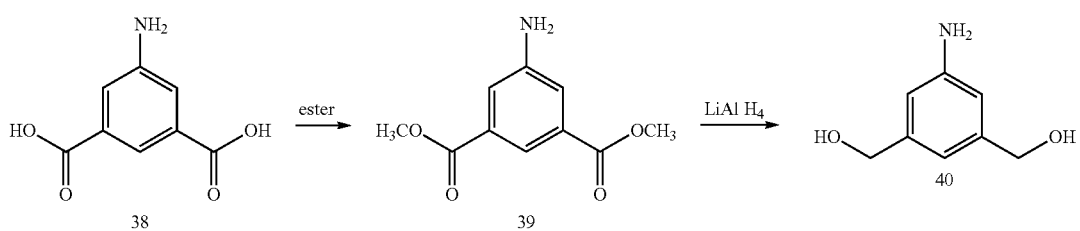

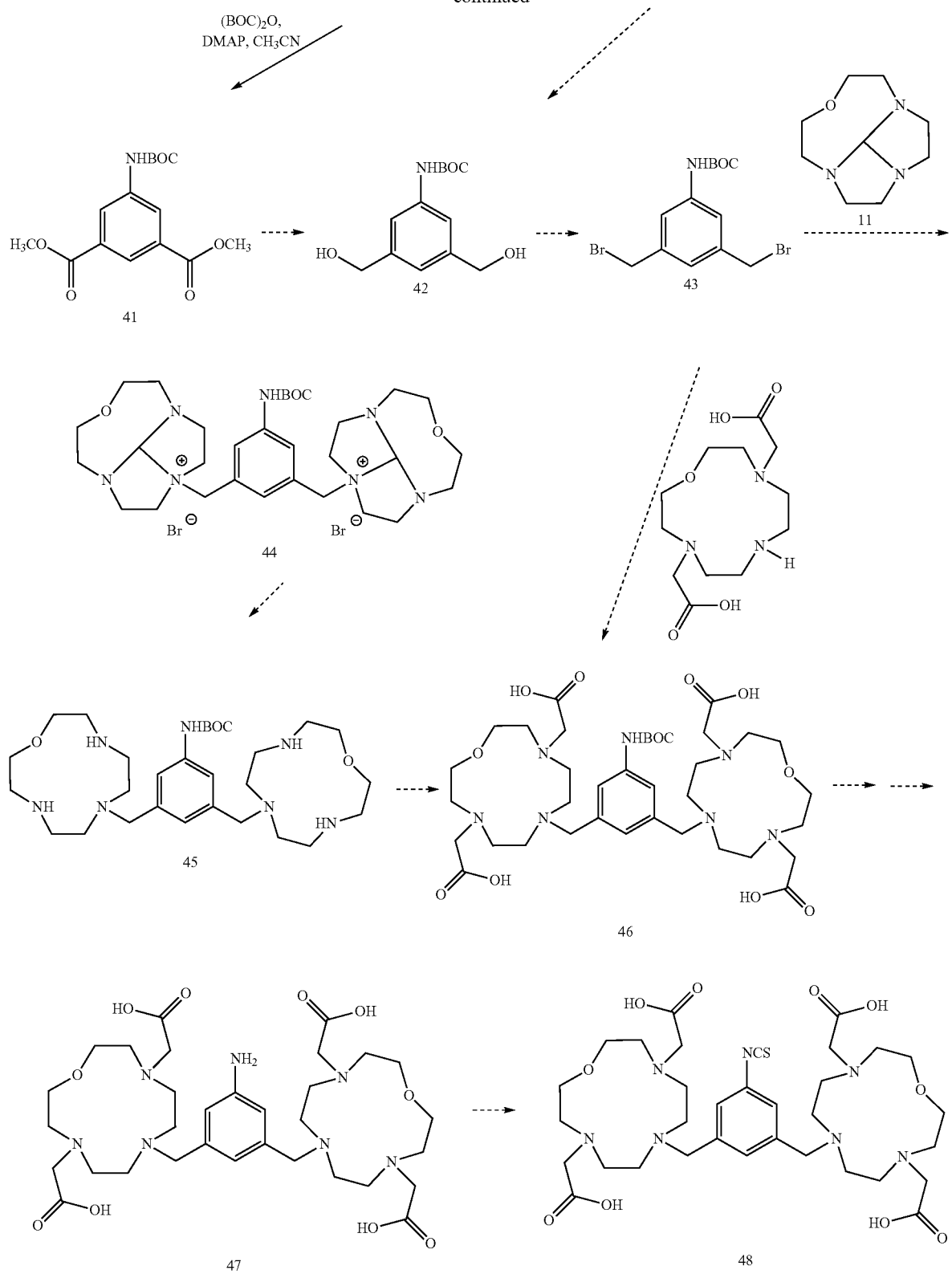

Metal complexes of compound 13, 14, or 19 are prepared as described below in Scheme 9. A zinc complex of Compound 13 is obtained by reacting zinc ion with Compound 13 under basic condition. The pH of the resulting reaction mixture is then adjusted to about pH 6.5 using a tetramethyl ammonium hydroxide solution to form zinc complex of compound 13. Metal complexes of compound 14 and 19 are prepared under the same condition.

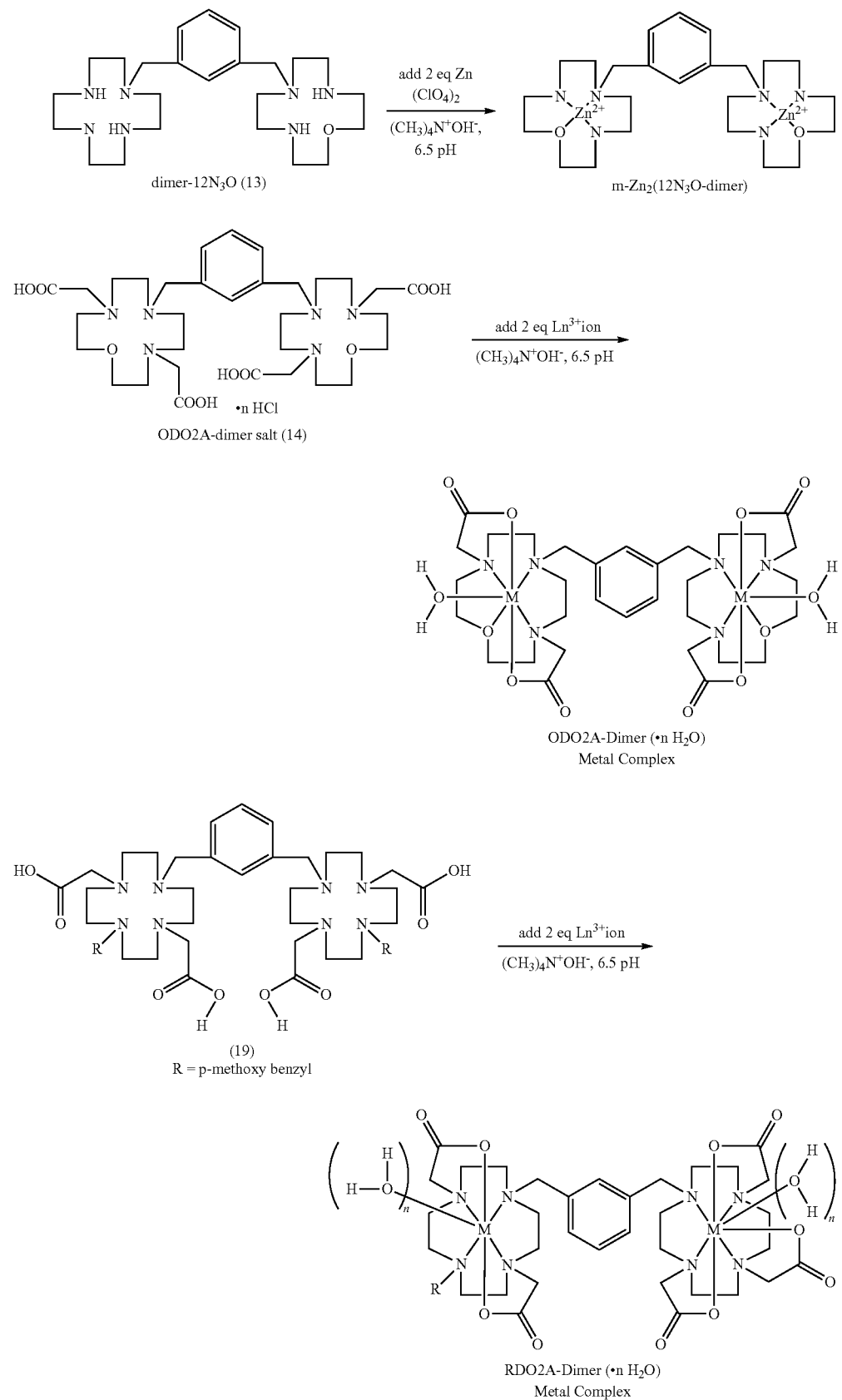

The methods provided in the present disclosure are simple and efficient to synthesize macrocyclic compounds of formula (I). The salts of compounds of formula (I) are stable and can be stored in inert atmosphere as these salts are hygroscopic in nature. In addition, the aromatic ring of compounds of formula (I) are connected directly to ring nitrogen of macrocyclic rings through the Linker $L_1$, $L_2$ or $L_3$. After chelating with the metal ion, this would allow a free rotation of the metal complex and reduced steric hindrance and strain-stress in the overall molecule. As a result, energy transfer from one metal ion to another metal ion via polar groups will become more efficient, thus enhancing the physicochemical properties of metal complexes. This will certainly improve biomedical applications of these metal complexes.

In the present disclosure, all technical and scientific terms herein used are having the same meaning as understood by ordinary skill person in the art, otherwise defined. The nomenclatures and procedures described herein are commonly employed in the laboratory practice. Standard techniques are used in synthesis and for chemical analysis ["Advanced Organic Chemistry: Reactions, Mechanisms and Structure" by March, $3^{rd}$ ed. (1985) John Willey & Sons, New York, N.Y.]

The synthesis of compounds of the present disclosure are illustrated by, but not limited to the following examples.

EXAMPLES

Example 1

Synthesis of Compound 4
(1,5-ditosyloxy-3-oxapentane)

Diethyleneglycol (10.61 g, 0.1 mol) was added into triethylamine (100 ml) and stirred with an overhead stirrer. To this mixture, tosylchloride (0.25 mol, 47.7 g) in ether (250 ml) was added slowly in 30 min at 0° C. The reaction mixture was stirred overnight at ambient temperature. The white solid precipitated in the reaction mixture was filtered and washed with water and then with a small amount of ether. The white solid was recrystallized from ethanol to afford compound 4 in 93% yield. mp: 88-89° C.; $^{13}$C NMR (CDCl$_3$, 300 MHz): δ 21.5, 68.6, 69.0, 127.8, 129.8, 132.6, 144.9.

Synthesis of Compound 5
(N,N',N"-tritosyldiethylenetriamine)

Diethylenetriamine (0.1 mol, 10.32 g) was added into a sodium hydroxide solution (0.33 mol, 100 mL) in a flask and stirred with an overhead stirrer. To this solution, tosylchloride (0.35 mol, 66.74 g) in ether (350 ml) was added dropwise using an addition funnel over 30 min at 0° C. The reaction mixture was stirred for 14-16 h at ambient temperature. The white precipitate was filtered and washed with water and then with ether. The crude product was recrystallized from ethanol to yield compound 5 in 88%. mp: 175; $^{13}$C NMR (CDCl$_3$, 300 MHz) δ 21.2, 41.8, 48.6, 126.8, 130.0, 135.4, 137.5, 143.9.

Synthesis of Compound 7 (12N$_3$Ts$_3$O)

Compound 4 (0.03 mol, 12.53 g) was dissolved in DMF and heated to 70° C. in a flask. Sodium hydride (4 equiv., 0.12 mol) was added slowly into a solution of compound 5 (0.03 mol, 17.00 g) in DMF in a beaker over 30 min at 0° C. to form sodium salt of compound 5. After the complete addition of sodium hydride, the reaction mixture was stirred for 15-20 min and then filtered under vacuum. The filtrate was added to the solution of compound 4 dropwise over a 30 min at 70° C. The reaction mixture was heated to 120° C. and stirred for ~16 h at this temperature. The pale yellow reaction mixture was concentrated. The resulting sticky residue was poured into water with strong stirring. The precipitated crude compound was filtered and then recrystallized from chloroform/ethanol to obtain compound as a white solid in 86% yield. mp 199-201° C.; $^{13}$C NMR (CDCl$_3$, 300 MHz): δ 21.5, 48.0, 50.5, 51.0, 72.0, 127.3, 129.8, 134.9, 143.7.

Synthesis of Compound 9 (12N$_3$O)

Concentrated sulphuric acid (100 ml) was added into compound 7 (0.04 mol, 25.55 g) at ambient temperature and the reaction mixture was heated to 140° C. for 1 day. Diethyl ether (300 ml) was added to the reaction mixture at 0° C. to wash the black solution twice or thrice to obtain a black sticky solid. The black sold was dissolved in water (100 ml) and was discolored by charcoal. After filtration, a colorless filtrate was obtained. The pH of the solution was adjusted to 12 or above 12 with a sodium hydroxide solution. This solution was extracted with chloroform 5 times, dried over magnesium sulfate, and then concentrated to obtain compound 9 as a white solid in 87% yield. mp 78-79° C.; $^1$H NMR (CDCl$_3$, 300 MHz): δ 2.53-2.56 and 2.66-2.75 (m, 12H, NCH$_2$), 3.50-3.54 (t, 4H, OCH$_2$); $^{13}$C NMR (CDCl3, 300 MHz): δ 46.1, 46.3, 66.3.

Synthesis of Compound 11 (12N$_3$O-tricyclic Form)

Compound 9 (0.03 mol, 5.22 g) was dissolved in toluene (90 ml) and heated to 60° C. under nitrogen. To this solution, dimethylformamide dimethyl acetal (0.03 mol, 3.57 g) was added slowly and the reaction mixture was stirred for 6 h at 60° C. The reaction mixture was concentrated and dried to get yellowish oily residue in 84% yield. $^1$H NMR (CDCl$_3$, 300 MHz): δ 2.6-2.8 (m, 12H, NCH$_2$), 3.3-3.4 (m, 4H, OCH$_2$), 4.7 (s, 1H, CH); $^{13}$C NMR (CDCl$_3$, 300 MHz) δ 51.7, 53.3, 53.8, 71.5, 100.8.

Synthesis of Compound 12 (Dimer-12N3O-tricyclic Form)

Compound 11, 12N$_3$O-tricyclic form (0.031 mol, 5.67 g) was dissolved in dry acetonitrile and heated to 50° C. under nitrogen. To above solution, the solution of m-dibromo xylene (0.0125 mol, 3.3 g) in dry acetonitrile (15 ml) was added dropwise. The reaction mixture was stirred for 6 h and the resulting white solid dibromide salt, compound 12 (12N$_3$O-tricyclic-dimer bromide salt) was obtained after filtration.

Synthesis of Compound 13 (Dimer-12N$_3$O)

Compound 12, dibromide salt, was refluxed in 80 ml sodium hydroxide (2 N) solution for 12 h. After cooling, the reaction mixture was extracted with chloroform for 5 times. The combined organic layer was dried over magnesium sulfate and concentrated to obtain a white solid of compound 12 in 94% yield. $^1$H NMR (CDCl$_3$, 300 MHz) δ 2.58, 2.63, 2.73 (three broad s, 24H, NCH$_2$), 3.53 (s, 4H, benzylic), 3.58 (s, 8H, OCH$_2$), 7.19-7.31 (m, 4H, aromatic); $^{13}$C NMR (CDCl$_3$, 300 MHz) δ 44.1, 46.2, 51.4, 59.2, 66.3, 128.1, 128.5, 130.1, 138.8.

Synthesis of Zinc Complex of Compound 13 (Dimer-12N₃O)

Compound 13 (Dimer-12N₃O) was chelating with copper and zinc ion to form respective metal ion complexes which was observed from the thermodynamics titration experiments.

Zinc perchlorate was added into aqueous solution of ligand and the pH of the solution was adjusted to 6.5 with tetraammonium hydroxide to obtain zinc complex. Standardization of ligand stock solution was carried out by complexing with $Cu^{2+}$ ion. Besides, protonation constants will also be known by titration raw data with calculation software—"Hyperquad 2008".

The formation of the complexes is shown in FIGS. 1A and 1B.

Experiment condition: [L']=1 mM, [M]=2 mM (for $M_2L'$), I=0.1 M with TMACl, at 25° C.

Example 2

Synthesis of Compound 14 (Dimer-ODO2A)

Compound 13 (Dimer-12N₃O) (5.7 mmol, 2.56 g) was dissolved in 40 ml of water and the pH of the solution was adjusted to 11 (or above 11) with sodium hydroxide solution. Bromoacetic acid (5 equiv.) was added to the above solution and the reaction mixture was stirred at 70° C. for 3 days. During the course of reaction, the pH of the reaction mixture was maintained above 11. After cooling the reaction mixture to room temperature, the pH was adjusted to 3.5 with hydrochloric acid and the solution was concentrated by rotavapor to obtain a pale yellow solid. The solid was dissolved in a minimum amount of water and purified by cation exchange resin to yield a pure white solid in 85% yield. $^1H$ NMR (CDCl₃, 200 MHz): δ 3.06 (m), 3.43 (m), 3.51 (m) (three m, 24H, $NCH_2$), 3.78-3.83 (m, 20H), 7.28 (m, 4H, aromatic); $^{13}C$ NMR (CDCl₃, 200 MHz): δ 45.9, 50.2, 54.5, 55.6, 57.2, 64.7, 130.1, 131.5, 132.7, 132.8, 168.0; Molecular ion peak $[M+1]^+=681$.

Synthesis of Lanthanide ion complex of Compound 14 (Dimer-ODO2A)

Compound 14 (Dimer-ODO2A) and lanthanide ion forms complexes in aqueous solution at a pH 6.5 which was adjusted by tetraammonium hydroxide. Standardization of ligand stock solution was carried out by complexing with $Ca^{2+}$ and $Zn^{2+}$ ions. Besides, protonation constants will also be known by titration raw data with calculation software—"Hyperquad 2008".

Figure 2:
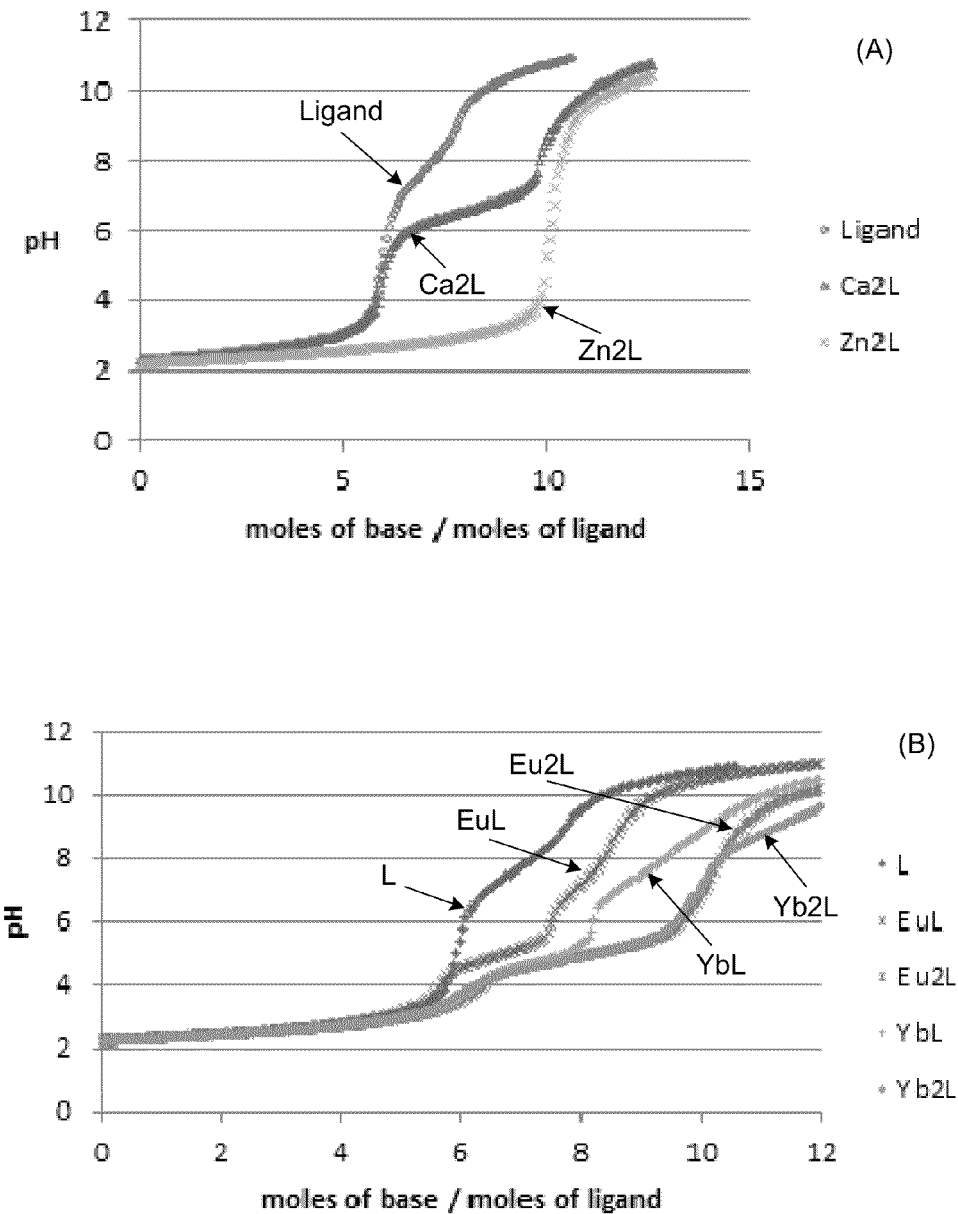
FIG. 2A is a graph showing titration curves of Dimer-ODO2A with $Ca^{2+}$ and $Zn^{2+}$ ions by standard base.
FIG. 2B is a graph showing titration curves of Dimer-ODO2A with Lanthanide metal (Eu and Yb) ions.

The formation of the complexes is shown in FIGS. 2A and 2B.

For calculation of stability constants of lanthanide metal (Eu, Yb) complexes: Experiment condition: [L]=1 mM, [M]=1 mM (for ML'), 2 mM (for $M_2L'$), I=0.1 M with TMACl, at 25° C.

Example 3

Synthesis of Compound 16 (Mono-$N_1$ alkylated cyclen)

Compound 15, cyclen glyoxal (1.58 g, 8.13 mmol) was dissolved in dry tetrahydrofuran (20 ml) under nitrogen atmosphere. To this solution, 4-methoxy benzyl chloride (1.18 g, 7.39 mmol) solution in THF (6 ml) was added dropwise. Then the reaction mixture was heated to 40° C. and stirred for 2 days. The white precipitated salt was washed several times with anhydrous THF and the resulting solid was dried under high vacuum to get compound 16 as a white solid (1.98 g) in 76% yield. $^1H$ NMR (200 MHz, D₂O): δ 7.42, 7.37, 7.01, 6.96 (4H, q, $C_6H_6$), 4.76, 4.72, 4.58, 4.49 (2H, d, —CHCH—), 3.87, 3.62 (2H, d, —$CH_2$-Aromatic), 3.75 (3H, s, —$OCH_3$), 3.48~2.37 (16H, m, —$NCH_2CH_2N$—); $^{13}C$ NMR (200 MHz, D₂O): δ 160.72, 134.11, 119.13, 114.91 ($C_{aromatic}$), 82.32, 71.68 ($C_{aminal}$), 61.10, 56.93, 55.52, 51.28, 48.32, 48.18, 47.60, 43.80 (—$NCH_2$).

Synthesis of Compound 17

Compound 16 (1.8 g, 5.13 mmol) was dissolved in dimethyl formamide (70 ml) at ambient temperature under argon atmosphere. The solution of m-xylene dibromide (0.658 g, 2.44 mmol) in DMF (25 ml) was added to above solution dropwise. After addition, the reaction mixture was heated at 45° C. for 4 days. Then the reaction mixture was centrifuged and the solid was collected and washed with a small amount of DMF and then with acetonitrile. The resulting solid was dried under vacuum to obtain a white solid in 50% yield. $^1H$ NMR (200 MHz, D₂O): δ 7.79~7.67, 7.48, 7.44, 7.04, 7.00 (12H, s, $H_{aromatic}$), 5.04~4.84 (4H, d, $H_{aminal}$), 4.81, 4.75 (4H, s, $CH_2$-Aromatic) 3.76 (6H, s, $OCH_3$) 3.50~2.88 (32H, m, $NCH_2CH_2N$); $^{13}C$ NMR (200 MHz, D₂O): δ 164.86, 135.84, 135.12, 133.98, 131.11, 127.94, 118.41, 115.03 ($C_{aromatic}$) 78.29, 77.21 ($C_{aminal}$) 61.04, 60.69, 60.08, 55.49, 54.45, 46.04, 42.70 ($NCH_2$).

Synthesis of Compound 18

Compound 17 (600 mg, 0.58 mmol) was dissolved in 4 ml hydrazine monohydrate and stirred under argon at 110° C. for 12 h. Then the reaction mixture was cooled to ambient temperature and filtered to remove excess hydrazine. The solid was collected and dissolved in 20 ml ethanol and concentrated by rotavapour. This process was repeated twice or thrice and then the solid was dried under high vacuum to obtain compound 18 in 95.3% (0.38 g). $^1H$ NMR (200 MHz, CDCl₃): 7.24~7.46, 6.88, 6.92 (Benzene, 12H), 3.79 (—$OCH_3$, 6H), 3.59, 3.57 (benzylic $CH_2$, 8H), 2.63 (—$NCH_2$, 32H); $^{13}C$ NMR (200 MHz, CD₃OD) 158.97, 139.19, 130.72, 130.11, 129.93, 126.73, 127.77, 123.48 ($C_{aromatic}$), 59.69, 59.06 ($NCH_2$-Aromatic,) 54.26 ($OCH_3$), 51.00, 50.83, 44.70 ($NCH_2$).

Synthesis of Compound 19 (Methoxybenzyl-DO2A-Dimer)

Compound 18, methoxybenzyl dimer12N4 (0.38 g, 0.55 mmol) was dissolved in dd water (30 ml) and pH of solution was adjusted to 11-12 with sodium hydroxide solution. To above solution, bromoacetic acid (0.46 g, 3.31 mmol) in 20 ml dd water was added slowly at 60° C. The reaction mixture was maintained at pH 11-12 for 3 days at 60° C. When the pH of the reaction mixture was not decreased (approximately after 3 days), the pH of the reaction mixture was adjusted to 4 with 6N hydrochloric acid solution. The reaction mixture was concentrated by rotavapor to get a solid residue, to which dry methanol (40 ml) was added. Sodium chloride was eliminated by filtration. The filtrate was concentrated and the residue was purified on cation exchange resin to obtain compound 19 (MB-DO2A-Dimer) as white solid in 70% yield. $^1H$ NMR (200 MHz, D₂O) δ: 7.50~7.60, 7.26~7.30, 6.83~6.87 (12H, s, Aromatic), 4.38, 4.22 (8H, s, Aromatic-$CH_2N$), 3.62 (6H, s, OCH₃) 2.88 (8H, s, CH₂COOH), 3.23, 2.80, 2.77 (32H, s, NCH₂CH₂N); $^{13}$C NMR (200 MHz, D₂O) δ 174.03 (—COOH), 160.40, 134.91, 133.33, 132.78, 131.01, 129.47, 120.53, 115.05 ($C_{Ar}$), 57.58 (NCH₂C₆H₆), 55.40 (CH₂COOH), 53.50 (OCH₃), 50.14, 49.87, 48.35 (NCH₂CH₂N).

Synthesis of Lanthanide Complexes of Compound 19 (Methoxybenzyl-DO2A-Dimer)

Compound 19 (Methoxybenzyl-DO2A-Dimer) and lanthanide ion forms complexes in aqueous solution at pH 6.5 which was adjusted by tetraammonium hydroxide. Standardization of ligand stock solution was carried out by complexing with $Ca^{2+}$ and $Zn^{2+}$ ions. Besides, protonation constants will also be known by titration raw data with calculation software—"Hyperquad 2008".

Figure 3:
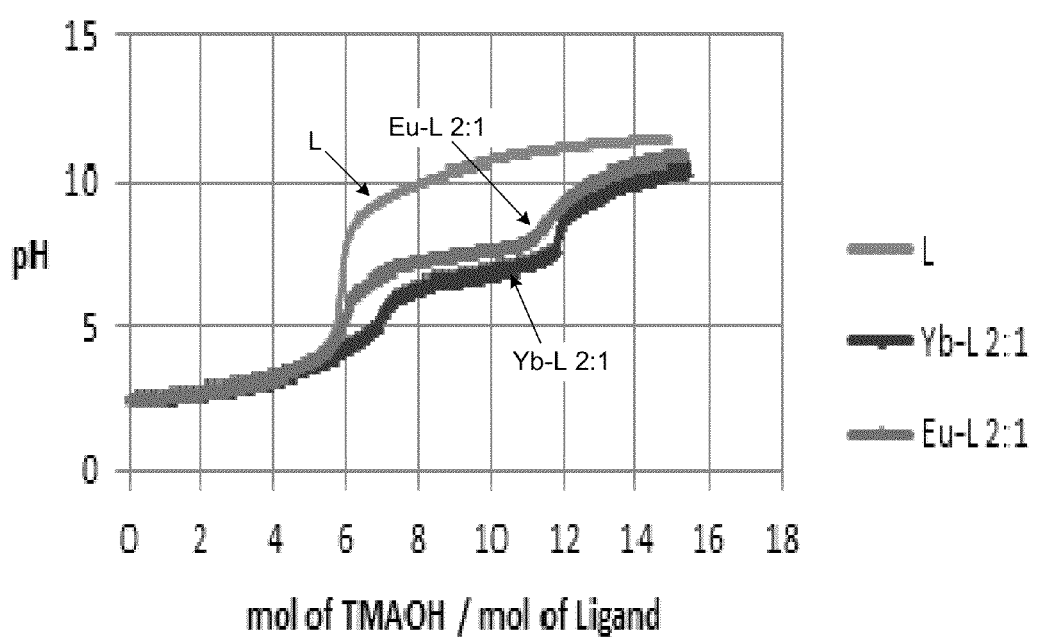
FIG. 3 is a graph showing titration curves of methooxy-benxyl-DO2A-Dimer with $Eu^{3+}$ and $Yb^{3+}$ ions.

FIG. 3 is a graph showing titration curves of methooxybenzyl-DO2A-Dimer with $Eu^{3+}$ and $Yb^{3+}$ ions.

For calculation of stability constants of lanthanide (Eu, Yb) complexes: Experiment condition: [L]=1 mM, [M]=1 mM (for ML'), 2 mM (for M₂L'), I=0.1 M with TMACl, at 25° C.

Example 4

Synthesis of Compound 20

Solution of m-xylene dibromide (0.618 g, 2.34 mmol) in dry acetonitrile (10 ml) was added dropwise to the solution of compound 15 (1 g, 5.15 mmol, 2.2 equiv.) in acetonitrile (20 ml) at ambient temperature under argon. The reaction mixture was stirred for 2.5 days. The white salt precipitate was washed several times with acetonitrile till washing was colorless. The white salt was dried under high vacuum to get 1.07 g of compound 20 (~100% yield). $^{1}$H NMR (200 MHz, D₂O) δ 2.35-2.6 (m, 2H), 2.6-3.0 (m, 8H), 3.0-3.35 (m, 10H), 3.35-3.6 (m, 8H), 3.73 (s, 2H), 4.0 (s, 2H), 4.15 (t, 2H), 4.66-4.96 (dd, 4H), 7.6-7.8 (m, 4H); $^{13}$C NMR (200 MHz, D₂O) δ 43.67, 47.52, 48.13, 48.24, 51.25, 56.97, 60.72, 61.39, 71.56, 8308, 128.4, 130.92, 134.99, 135.98.

Synthesis of Compound 21

Compound 15, cyclen glyoxal (3.35 g, 17.24 mmol) was dissolved in 42 ml anhydrous tetrahydrofuran under nitrogen atmosphere. To this solution, methyl iodide (1.07 ml, 16.89 mmol) solution in tetrahydrofuran (14.5 ml) was added dropwise at ambient temperature. The reaction mixture was stirred at same temperature for 2 days. The mono-salt precipitate was filtered and washed with dry tetrahydrofuran, dried under high vacuum to obtain compound 21 as a white solid in 72.59% yield (4.12 g). $^{1}$H NMR (200 MHz, D₂O) δ 3.43~3.85, 3.07~3.24, 2.67~2.86, 2.37~2.46 (18H, mCHCH and NCH₂) 3.27 (3H, s, CH₃); $^{13}$C NMR (200 MHz, D₂O) δ 83.44, 71.51 (—CHCH—) 65.43, 61.07, 51.22, 48.26, 48.08, 47.79, 44.04 (—NCH₂) 47.60 (CH₃).

Synthesis of Compound 22 (by Method A, Scheme 3)

Compound 20 (70 mg, 0.107 mmol) was dissolved in dimethyl formamide (2.5 ml) under argon. To this solution, methyl iodide (0.1 ml, in excess) was added at ambient temperature and the reaction mixture was stirred at ambient temperature for 4 days. Then acetonitrile (20 ml) was added to the stirred reaction mixture slowly. The precipitate was washed with acetonitrile several times till washing was colorless. Tetra-salt product was dried under high vacuum to obtain 50 mg of compound 22 in 58% yield.

Synthesis of Compound 22 (by method B, Scheme 4)

Compound 21 (4.07 g, 12.1 mmol) was dissolved in 40 ml DMF under nitrogen atmosphere, to which m-xylene dibromide (1.56 g, 5.764 mmol) in DMF (13 ml) was added dropwise at ambient temperature. The reaction mixture was stirred at room temperature for 2 days. The tetra-salt precipitate was centrifuged and washed once with a small amount of DMF and then washed with acetonitrile several times. The white solid salt (compound 22) was dried under high vacuum to obtain compound 22 in 54% yield (3.49 g). $^{1}$H NMR (200 MHz, D₂O) δ 7.70~7.86 (4H, $H_{Aromatic}$), 4.75ƒ5.06 (4H, CHCH), 4.68 (4H, Aromatic-CH₂), 3.38 (6H, —CH₃), 4.2~4.36, 3.80~4.05, 3.31~3.63, 2.93~3.20 (—NCH₂); $^{13}$C NMR (200 MHz, D₂O) δ 134.83, 134.14, 130.16, 126.86 ($C_{aromatic}$), 76.97 ($C_{aminal}$), 45.08 (—CH₃), 63.86, 60.11, 59.21, 58.01, 53.53, 45.55, 45.29, 41.92, 41.59 (—NCH₂).

Synthesis of Compound 23

Compound 22 (3.35 g, 2.82 mmol) was heated with hydrazine monohydrate (20 ml) at 110° C. in argon. After cooling, the precipitate was filtered and remaining hydrazine was removed by rotatory evaporator as an azotropic mixture using ethanol as the solvent. The same procedure was repeated twice. The resulting product was dried under high vacuum to obtain white oil (1.25 g, 93%). The white oil was further treated with hydrochloric acid (6 N) at 0° C. to convert it to HCl salt form, compound 23. $^{1}$H NMR (HCl salt form, 200 MHz, D₂O) δ 7.39, 7.36, 7.27, 7.23 (4H, m, Aromatic H), 3.78 (4H, s, Benzylic-CH₂), 2.77~3.15 (32H, m, NCH₂), 2.26 (6H, s, CH₃); $^{13}$C NMR (HCl form, 200 MHz, D₂O) δ 133.13, 132.73, 131.01, 129.53 ($C_{Aromatic}$), 57.52 ($C_{Benzylic-c}$), 51.43, 48.30, 42.41, 42.31 (—NCH₂) 42.64 (CH₃).

Synthesis of Compound 24

Compound 23 (1.93 g, 2.62 mmol) was dissolved in 55 ml dd water and basified with an aqueous sodium hydroxide solution until the pH reached 11-12. To this solution, an aqueous solution of bromoacetic acid (2.2 g, 15.86 mmol) in 30 mL dd H₂O was added slowly. The reaction mixture was heated at 60° C., and the pH of the reaction mixture was maintained at 11-12 by using the sodium hydroxide solution. After 3 days, the reaction mixture was acidified using hydrochloride (6 N) till the pH of the mixture reached 4. The solvent was removed by rotatory evaporator. The residue was dissolved in anhydrous methanol (40 ml) and the mixture was filtered to remove sodium chloride salt. The filtrate was evaporated and the resulting solid was purified on cation exchange resin to obtain compound 24 as a white solid in 70% yield (1.75 g). $^{1}$H NMR MHz, D₂O) δ 7.49, 7.42 (4H, s, Aromatic), 4.42 (4H, s, benzylic CH₂), 2.97~3.40 (40H, m, NCH₂ CH₂COOH), 2.83 (6H, s, CH₃), $^{13}$C NMR (400 MHz, D₂O) δ 174.66 (—COOH), 133.90, 132.97, 131.51, 130.17 ($C_{aromatic}$), 56.90 (benzene-CH2), 52.98 (CH₂COOH), 54.50, 50.61, 49.08, 48.69 (NCH₂), 43.14 (CH₃).

Synthesis of Compound 30

In a solution of pyridine-2,6-dicarboxylic acid (compound 29, 10 g, 59.8 mmol) in 100 ml methanol (ACS grade) under argon, thionyl chloride (8 ml, 109 mmol) was added slowly at 0-5° C. The reaction mixture was refluxed for 18-20 hrs, and then cooled to ambient temperature and then to 0° C. Compound 30 was crystallized out from the solution. The solid was filtered under vacuum and washed with cold methanol (30 ml). The resulting solid was dried to get 9.3 g of compound 30 (80%). MP=122° C.; $R_f$=0.61 in ethyl acetate; $^1$H NMR (200, CDCl$_3$) δ 3.98 (s, 6H, ester CH$_3$), 7.98 (t, 1H, γ proton of pyridine ring), 8.26 (d, 2H, β protons of pyridine ring).

Synthesis of Compound 31

In a solution of compound 30 (9.3 g, 47.7 mmol) in methanol (200 ml) at 0° C. under argon, sodium borohydride (6.32 g, 166.3 mmol) was slowly. The reaction mixture was stirred at 0° C. for 3 hrs. Reaction was monitored by TLC. Saturated sodium bicarbonate was added to decompose sodium borohydride. The reaction mixture was concentrated and the solution was extracted with chloroform (3×200 ml). The organic layers were combined and dried over magnesium sulphate. After removing solvent, the white residue was purified on silica gel column (60 g) using 30-40% ethyl acetate/chloroform as eluent to obtain compound 31 (4.5 g, 56%). MP=83° C.; $R_f$=0.38 in ethyl acetate; $^1$H NMR (200, CDCl$_3$) δ 3.90 (s, 3H, OCH$_3$), 4.36 (br s, 1H, OH), 4.79 (s, 2H, CH2), 7.5 (d, 1H, Ar—H), 7.76 (t, 1H, γ proton of pyridine ring), 7.93 (d, 1H, Ar—H).

Synthesis of Compound 32

Into a solution of compound 31 (6.4 g, 38.32 mmol) in chloroform (50 ml) at 0° C. under argon, phosphorous tribromide (6 ml, 63 mmol) was added slowly. Then the reaction mixture was stirred at ambient temperature for 14-16 hrs. The reaction was quenched with a 20% potassium carbonate solution at 0° C. till pH=8-9. The reaction mixture was extracted with chloroform. The organic layer was dried over magnesium sulphate. After removing the solvent, the residue was purified on silica gel column using chloroform as eluent. Compound 32 was obtained in 6.5 g (70%). $R_f$=0.60 (in 3:1 hexane:ethyl acetate). $^1$H NMR (200, CDCl$_3$) δ 4.01 (s, 3H, OCH3), 4.65 (s, 2H, benzylic protons), 7.71 (d, 1H, ArH), 7.87 (t, 1H, ArH), 8.04 (d, 1H, ArH); $^{13}$H NMR (200, CDCl$_3$) δ 33.01, 52.87, 124.25, 126.93, 138.02, 147.45, 157.23, 165.15.

What is claimed is:

1. A compound of formula (I):

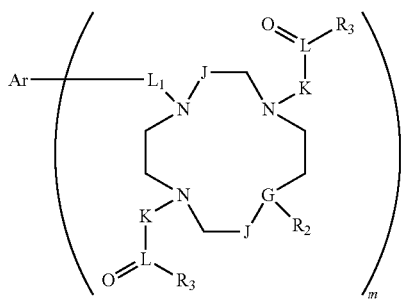

(I)

or an enantiomer, a tautomer, a pharmaceutically acceptable salt, or a prodrug thereof;
wherein:
Ar is an optionally substituted phenyl ring or a pyridine ring;
G is O or S;
J is —CH$_2$—, or —CH$_2$CH$_2$—;
L$_1$ is —CH$_2$—, or —CH$_2$CH$_2$—;
K is —CH$_2$—, or —CH$_2$CH$_2$—;
L is —C—, —S(O)—, or —P(OH)—;
each R$_2$ is absent;
each R$_3$ is independently —OH, or —NHR$_6$;
each R$_6$ is independently H, optionally substituted alkyl, optionally substituted alkenyl, optionally substituted alkynyl, optionally substituted aryl, or optionally substituted heterocyclic;
m is 2.

2. The compound of claim 1, wherein the compound of formula (I) is a compound of formula (II):

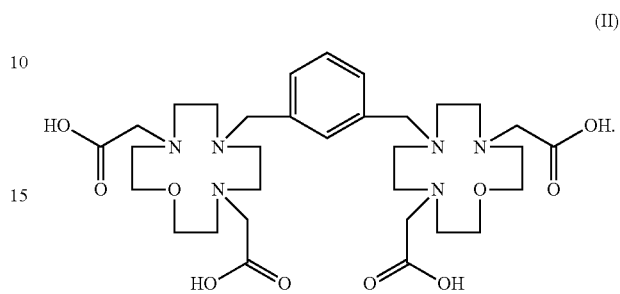

(II)

3. The compound of claim 1, further comprising at least one group of formula (IV):

—W—(X$_s$—Y$_t$)$_p$—   (IV)

that binds to Ar of the compound of formula (I) and to a biomolecule,
wherein:
W is —CH$_2$—, —SO—, —SO$_2$—, —CO—, —NHNH—, —CONH—, —NHCO—, —NH-CONH—, —CONHCO—, —NHCONHO—, —COO—, —COCH$_2$—, —CH$_2$CO—, —NHO—, —ONH—, —CH═CH—, —NH—, —NR$_8$, —NH(C═NH)NH—, —CH═N—, N═CH—, —SO$_2$NH—, —NHSO$_2$—, —NH—CS—, —NHC-SNH—, —NH(C═NH)NH—O—, —OCO—, —S—S—, or —N═N—,
R$_8$ is alkyl, cycloalkyl, or aryl;
X and Y are same or different and independently optionally substituted alkyl, cycloalkyl, aryl, or heterocyclic; and
s, t, and p are an integer from 0 to 100.

4. The compound of claim 3, wherein X and Y further comprises negatively charged carboxylate or positively charged ammonium moieties.

5. The compound of claim 3, wherein the biomolecule is a protein, an oligopeptide, an oligonucleotide, a modified oligopeptide or oligonucleotide, or a polymer.

6. The compound of claim 5, wherein the modified oligopeptide or oligonucleotide is phosphoroamidate, phosphoromonothioate, or phosphorodithioate, and wherein the polymer is polyethylene glycol or polylysine.

7. A pharmaceutical composition, comprising a pharmaceutically acceptable carrier and a compound of formula (I) or a metal complex of a compound of formula (I):

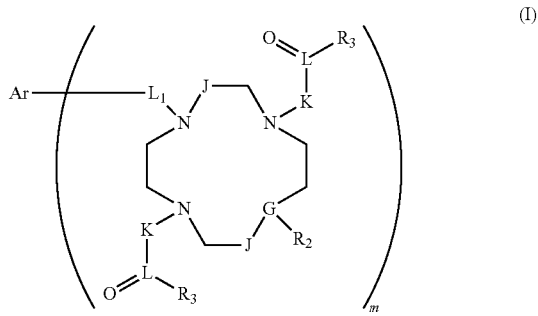

(I)

or an enantiomer, a tautomer, a pharmaceutically acceptable salt, or a prodrug thereof;

wherein:
Ar is an optionally substituted phenyl ring or a pyridine ring;
G is O or S;
J is —CH$_2$—, or —CH$_2$CH$_2$—;
L$_1$ is —CH$_2$—, or —CH$_2$CH$_2$—;
K is —CH$_2$—, or —CH$_2$CH$_2$—;
L is —C—, —S(O)—, or —P(OH)—;
each R$_2$ is absent;
each R$_3$ is independently —OH, or —NHR$_6$;
each R$_6$ is independently H, optionally substituted alkyl, optionally substituted alkenyl, optionally substituted alkynyl, optionally substituted aryl, or optionally substituted heterocyclic;
m is 2.

8. The pharmaceutical composition of claim 7, wherein the compound of formula (I) further comprises at least one group of formula (IV):

 (IV)

that binds to Ar of the compound of formula (I) and to a biomolecule,
wherein:
W is —CH$_2$—, —SO—, —SO$_2$—, —CO—, —NHNH—, —CONH—, —NHCO—, —NH-CONH—, —CONHCO—, —NHCONHO—, —COO—, —COCH$_2$—, —CH$_2$CO—, —NHO—, —ONH—, —CH=CH—, —NH—, —NR$_8$, —NH(C=NH)NH—, —CH=N—, —N=CH—, —SO$_2$NH—, —NHSO$_2$—, —NH—CS—, —NHCSNH—, —NH(C=NH)NH—O, —OCO—, —S—S—, or —N=N;

R$_8$ is alkyl, cycloalkyl, or aryl;

X and Y are same or different and independently optionally substituted alkyl, cycloalkyl, aryl, or heterocylic; and s, t, and p are an integer from 0 to 100.

9. The pharmaceutical composition of claim 8, wherein X and Y further comprises negatively charged carboxylate or positively charged ammonium moieties.

10. The pharmaceutical composition of claim 8, wherein the biomolecule is a protein, an oligopeptide, an oligonucleotide, a modified oligopeptide or oligonucleotide, or a polymer.

11. The pharmaceutical composition of claim 10, wherein the modified oligopeptide or oligonucleotide is phosphoroamidate, phosphoromonothioate, or phosphorodithioate, and wherein the polymer is polyethylene glycol or polylysine.

* * * * *